US005942214A

United States Patent [19]
Lucas et al.

[11] Patent Number: 5,942,214
[45] Date of Patent: *Aug. 24, 1999

[54] METHODS FOR CONTROLLING ENVIRONMENTAL ODORS ON THE BODY USING COMPOSITIONS COMPRISING UNCOMPLEXED CYCLODEXTRINS AND PERFUME

[75] Inventors: Juliet Marie Lucas, Cincinnati; Toan Trinh, Maineville; Michael Thomas Dodd, Mason; Robert Gregory Bartolo, Cincinnati, all of Ohio

[73] Assignee: The Procter & Gamble Company, Cincinatti, Ohio

[ * ] Notice: This patent is subject to a terminal disclaimer.

[21] Appl. No.: 08/871,166

[22] Filed: Jun. 9, 1997

[51] Int. Cl.$^6$ ............................ A61K 7/32; A61K 25/00; A61K 33/10; A61K 33/24; A61L 9/01
[52] U.S. Cl. ............................ 424/65; 422/5; 424/67; 424/69; 424/76.1; 424/76.2; 424/76.21; 424/76.4; 424/76.8; 424/78.03; 424/405; 424/642; 424/715; 424/717
[58] Field of Search ............................ 424/65, 76.1, 76.2, 424/76.21, 76.4, 76.8, 78.03, 642, 405, 715, 717; 422/5

[56] References Cited

U.S. PATENT DOCUMENTS

| | | | |
|---|---|---|---|
| 2,544,093 | 3/1951 | Kilgore | 252/1 |
| 3,074,891 | 1/1963 | Kulka | 252/305 |
| 4,278,658 | 7/1981 | Hooper et al. | 424/65 |
| 4,382,079 | 5/1983 | Marschner | 424/65 |
| 4,822,602 | 4/1989 | Sabatelli | 424/65 |
| 4,904,524 | 2/1990 | Yoh | 428/311.3 |
| 5,429,628 | 7/1995 | Trinh et al. | 604/359 |
| 5,486,355 | 1/1996 | Berschied, Jr. | 424/65 |
| 5,512,199 | 4/1996 | Khan et al. | 252/106 |
| 5,514,367 | 5/1996 | Lentini et al. | 424/59 |
| 5,518,727 | 5/1996 | Lajoie et al. | 424/400 |
| 5,540,853 | 7/1996 | Trinh et al. | 510/101 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Panitch | 424/65 |
| 5,663,134 | 9/1997 | Trinh et al. | 510/406 |
| 5,670,475 | 9/1997 | Trinh et al. | 510/470 |

FOREIGN PATENT DOCUMENTS

| | | |
|---|---|---|
| 0 613 675 A1 | 9/1994 | European Pat. Off. . |
| 2201880 | 5/1974 | France . |
| 2731520 | 1/1979 | Germany . |
| 208482 | 8/1992 | Hungary . |
| 53-41440 | 4/1978 | Japan . |
| 58-124452 | 7/1983 | Japan . |
| 61-128973 | 6/1986 | Japan . |
| 63-164953 | 7/1988 | Japan . |
| 3-170415 | 7/1991 | Japan . |
| 3-284616 | 12/1991 | Japan . |
| 5-269185 | 10/1993 | Japan . |
| WO 95/17175 | 6/1995 | WIPO . |
| WO 96/04940 | 2/1996 | WIPO . |

OTHER PUBLICATIONS

T. Loftsson, et al. "Interactions Between Preservatives and 2–Hydroxypropl–β–Cyclodextrin", Drug Development and Industrial Pharmacy, 18(13), 1992, pp. 1477–1484.

Hashimoto, H., "Studies on the Industrial Production and Application of Cyclodextrins", Starch Science, vol. 36, No. 1 (1989), pp. 35–42.

H. Matsuda, et al., "Application of 2–Hydroxypropyl–β–Cyclodextrin to Perfumes and Cosmetics", The 7th International Cyclodextrins Symposium, Tokyo, Japan, Apr. 25–28, 1994, pp. 516–519.

Hashimoto, H., "Application of Cyclodextrins to Foods, Toiletries and Other Products in Japan", Ensuiko Sugar Refining Co., Ltd., pp. 13–46, No date.

U.S. application No. 08/736,469, Trinh et al., filed Oct. 24, 1996.

U.S. application No. 08/736,093, Trinh et al., filed Oct. 24, 1996.

U.S. application No. 08/889,607, Trinh et al., filed Jul. 8, 1997.

U.S. application No. 08/736,471, Lucas et al., filed Oct. 24, 1996.

U.S. application No. 08/736,470, Lucas et al., filed Oct. 24, 1996.

U.S. application No. 08/738,964, Dodd et al., filed Oct. 24, 1996.

U.S. application No. 08/736,838, Peterson et al., filed Oct. 28, 1996.

U.S. application No. 08/739,091, Peterson et al., filed Oct. 28, 1996.

U.S. application No. 08/871,854, Lucas et al., filed Jun. 9, 1997.

U.S. application No. 08/871,791, Dodd et al., filed Jun. 9, 1997.

U.S. application No. 08/871,855, Trinh et al., filed Jun. 9, 1997.

U.S. application No. 08/871,853, Lucas et al., filed Jun. 1997.

U.S. application No. 08/871,857, Lucas et al., filed Jun. 9, 1997.

(List continued on next page.)

Primary Examiner—Shelley A. Dodson
Attorney, Agent, or Firm—Kristen K. Stone; Mary Catherine Hentz

[57] ABSTRACT

The present invention encompasses a method of controlling environmental odors on the body comprising the application to the skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants; from about 0.004% to about 2%, by weight of the composition, of a hydrophilic, volatile perfume composition; and an aqueous carrier. The compositions can be applied directly as a spray, poured from a bottle and applied by hand, or applied via a wipe.

18 Claims, No Drawings

U.S. PATENT DOCUMENTS

U.S. application No. 08/871,790, Peterson et al., filed Jun. 9, 1997.
U.S. application No. 08/871,856, Peterson et al., filed Jun. 9, 1997.
U.S. application No. 08/871,858, Lucas et al., filed Jun. 9, 1997.
U.S. application No. 08/871,577, Lucas et al., filed Jun. 9, 1997.
U.S. application No. 08/871,860, Lucas et al., filed Jun. 9, 1997.
U.S. application No. 08/871,861, Peterson et al., filed Jun. 9, 1997.
U.S. application No. 08/871,092, Peterson et al., filed Jun. 9, 1997.
U.S. application No. 08/289,732, Trinh et al., filed Aug. 12, 1994.
U.S. application No. 08/289,733, Trinh et al., filed Aug. 12, 1994.
U.S. application No. 08/289,734, Cappel et al., filed Aug. 12, 1994.
U.S. application No. 08/289,735, Cappel et al., filed Aug. 12, 1994.
U.S. application No. 08/289,969, Pilsof et al., filed Aug. 12, 1994.
U.S. application No. 08/871,576, Woo et al., filed Jun. 9, 1997.
U.S. application No. 08/871,119, Woo et al., filed Jun. 9, 1997.
U.S. application No. 08/871,042, Woo et al., filed Jun. 9, 1997.

METHODS FOR CONTROLLING ENVIRONMENTAL ODORS ON THE BODY USING COMPOSITIONS COMPRISING UNCOMPLEXED CYCLODEXTRINS AND PERFUME

BACKGROUND OF THE INVENTION

Daily contact with substances which leave unpleasant and/or lingering odors on an individual's body and hair is almost unavoidable. Foods such as fish, onions, garlic or other spices, cooking odors, smoke, tobacco, and gasoline are just a few of the common environmental sources of malodors in daily life.

Numerous attempts have been made to conceal unpleasant odors through the use of deodorizing compositions. These compositions typically rely on the presence of heavy fragrances or perfumes to mask odors. However, perfumes and fragrances alone are often inadequate at fully concealing malodors, and some may be irritating to the user.

Zeolites such as those marketed under the trade name Abscents® by the Union Carbide Corporation and UOP are known odor absorbers. However these commonly known solid odor absorbers, in addition to known activated charcoal odor absorbers, lose functionality when wet. Therefore, when wetted by body fluids or when carried in an aqueous solution, these odor absorbers are not preferred as they substantially lose their desired odor absorbent characteristics. Furthermore, zeolites can cause a "harsh" feel if too much is deposited onto the skin. The white zeolite powder and the black activated charcoal can also be rather visible and unsightly when applied to surfaces such as skin.

U.S. Pat. No. 5,534,165, to Pilosof et al., issued Jul. 9, 1996, describes aqueous, odor absorbing compositions for controlling odors on fabrics, particularly clothes. Such compositions, however, are not for use directly on the human skin.

Thus, there remains a need for improved methods for controlling odors which are safe and effective for use on the entire body. Furthermore, it is desirable that the perfume is fleeting such that it indicates freshness, but is not long lasting on the user's skin. More particularly, there is a need for convenient methods of absorbing a broad spectrum of odors that are not fully suppressed by the aforementioned means.

It has been discovered that methods for such enhanced malodor control can be safely provided to the entire body by application of a leave-on mixture which incorporates odor absorbing, uncomplexed cyclodextrins and a hydrophilic, volatile perfume composition. Such methods provide a leave-on mixture with optimal malodor absorbing characteristics. Moreover, it has been discovered that the aforementioned benefits may be delivered in a mixture which also optionally delivers skin aid benefits to the user such as protection and/or moisturization.

These and other objects of the present invention will become readily apparent from the detailed description which follows. All percentages, ratios, and parts herein, in the Specification, Examples, and claims are by weight unless otherwise stated. The term "g", as used herein, means gram. The term "ml", as used herein, means milliliter. The term "wt.", as used herein means weight.

SUMMARY OF THE INVENTION

The present invention encompasses a method of controlling environmental malodors on skin comprising the application to the skin of a composition comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, and skin protectants; one or more surfactants; from about 0.004% to about 2%, by weight of the composition, of a hydrophilic, volatile perfume composition; and an aqueous carrier.

DETAILED DESCRIPTION OF THE INVENTION

The methods for controlling environmental malodors of the present invention comprise the application of a malodor-absorbing composition comprising solubilized, water-soluble, uncomplexed cyclodextrin and a hydrophilic, volatile perfume composition. The invention compositions can be applied directly as a spray, poured from a bottle and applied by hand, or applied via a pre-formed wipe which is wet with the composition when it is applied to skin and/or hair. The present invention also relates to an article of manufacture comprising the environmental odor-absorbing composition incorporated into a flexible dispensing means.

The term "environmental malodors", as used herein means any odor which may be on a human or mammal which is not the result of human or mammalian body odor and/or body fluids. Such odors include but are not limited to odors from foods such as fish, garlic, onions, peppers and spices; cooking; smoke; tobacco; gasoline; and the like.

The term "body fluids", as used herein, includes eccrine sweat, apocrine sweat, sebum, build up of sensible moisture from transepidermal water loss, vaginal discharge, urine, and mixtures thereof. The term "body odor", as used herein, means odors which are generated as a result of the natural functioning of a human or mammalian body. Such odors include, but are not limited to odors produced by microorganisms of the human or mammalian skin (i.e. bacterial decomposition of skin secretions), urine, or vaginal discharge, and mixtures thereof. The term "entire body" means the entire external surface of human or mammalian skin. The term "skin" means human or mammalian skin.

A detailed description of essential and optional components of the present invention is given below.

METHODS OF USE

The present invention encompasses a method of controlling environmental malodors on skin comprising the application to skin of a composition comprising from about 0.1% to about 5%, by weight of the composition, of solubilized, water-soluble, uncomplexed cyclodextrin; from about 0.004% to about 2%, by weight of the composition, of a hydrophilic, volatile perfume composition, from about 0.1% to about 36%, by weight of the composition, of an oil phase selected from the group consisting of emollients, moisturizers, and skin protectants; one or more surfactants; and an aqueous carrier. These compositions may also optionally comprise one or more of the following: hydrophobic antimicrobials; water-soluble antimicrobial preservatives; low molecular weight polyols; zinc salts; water-soluble polymers; soluble carbonate and/or bicarbonate salts; chelating agents; zeolites; activated carbon; and mixtures thereof.

An "effective amount" of the compositions of the present invention, as used herein, means an amount sufficient to absorb odor to the point that it is less noticeable by the human sense of smell. While the determination of an effective amount used and the number of uses per day is ultimately left to the discretion of the user, typically an effective amount will be from about 0.05 grams to about 3.0 grams of environmental odor absorbing composition per use, applied from about 1 to about 15 times per day, for as many days as desired by the user.

The compositions of the present invention are topically applied directly to the skin or hair. The compositions can be delivered by placing the composition into a dispensing means and applying an effective amount via spraying or rubbing the composition onto the desired skin surface; typically the entire body. Preferably the dispensing means is a wipe or a spray dispenser. Distribution of the composition of the present invention can also be achieved by using a pre-formed applicator such as a roller, pad, sponge, tissue, cotton ball, hand, etc.

Alternatively, the user may combine the composition of the present invention with a wipe substance of his or her own choosing. To do this, the user simply chooses a wipe substance such as a commercial paper towel, tissue, sponge, cotton, pad, washcloth, or the like; and pours, from a bottle or other suitable container, a solution of the composition of the present invention over the chosen wipe substance and applies the composition to the desired area of the body. In this manner, the user may use as much or as little of the composition of the present invention as he/she desires, depending upon their intended use and degree of odor control necessary.

Cyclodextrin

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Non-derivatised beta-cyclodextrin can be present at a level up to its solubility limit of about 1.85% at room temperature. When beta-cyclodextrin is applied to a wipe substrate, levels higher than its solubility limit can be used.

Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The preferred highly water-soluble cylcodextrins are hydroxy propyl beta-cyclodextrin and methylated beta-cyclodextrin.

It is also preferable to use a mixture of cyclodextrins. Such mixtures absorb environmental odors on the body more broadly by complexing with a wider range of odoriferous molecules having a wider range of molecular sizes. Preferred are mixtures of beta-cyclodextrin and/or its derivatives with alpha-cyclodextrin and/or its derivatives, and mixtures thereof The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 10%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with fluids. This is convenient for the user because the cyclodextrins, while on dry skin, will not readily fill their cavities with other odors which would otherwise render them less efficient. More particularly, upon solubilization of the cyclodextrins by body fluids or other fluids, the isolated cavities again become available to form inclusion complexes with the environmental odor molecules on the body. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

Oil Phase

The present invention method also includes compositions comprising an oil phase. The oil phase is chosen from the following ingredients: skin protectants, emollients, and/or moisturizers. Saturated or hydrogenated oils are preferred. These ingredients enhance the skin feel characteristics and/ or skin care benefits of the present invention. Additionally, the oil phase provides a medium in which hydrophobic antibacterials, if present, may be dissolved.

Skin protectant ingredients can prevent or reduce chafing, skin irritation and/or skin friction that may occur between skin-to-skin contact sites. Preferred skin protectants useful in the present invention include, but are not limited to: vitamin A, cod liver oil, cocoa butter, shark liver oil, dimethicone, petrolatum, white petrolatum, mineral oil, jojoba oil, and lanolin. More preferred are dimethicone, petrolatum, white petrolatum, mineral oil, jojoba oil, and lanolin. Most preferred is dimethicone.

Moisturizers can aid in adding moisture to the skin may be included in the oil carrier of the present invention. Preferred moisturizers useful in the present invention include, but are not limited to vegetable oils and mineral oil. More preferred are hydrogenated or saturated vegetable or mineral oils. Other moisturizers useful in the present invention can be chosen from the oily moisturizers in *Cosmetic Bench Ref.* 1994, pages 46–48, incorporated herein by reference.

Emollients for softening and soothing of skin are also useful in the present invention. Emollients useful herein include tocopherol or tocopherol acetate, triglycerides, vegetable oils, or mineral oil. Other emollients useful in the present invention can be chosen from the oily emollients in *Cosmetic Bench Ref.* 1994, pages 27–31, incorporated herein by reference.

The oil phase or carrier of the present invention is present at an "effective level" which is a level which provides the desired skin benefits of the particular ingredients. Typically, the oil phase is present at a level of from about 0.1% to about 36%, preferably from about 0.2% to about 6%, by weight of the composition.

Surfactant

A surfactant must be used in the present invention. Surfactants are known in the art of forming oil-in-water emulsions. Preferably, a combination of surfactants are used for improved stability. Surfactants useful herein are nonionic surfactants, anionic surfactants, cationic surfactants, amphoteric surfactants, zwitterionic surfactants, detersive surfactants and mixtures thereof. When a surfactant containing one, or more, aliphatic alkyl group is used, it is preferred that it contain relatively short alkyl chains of from about 5 to about 14 carbon atoms.

Suitable nonionic surfactants are fatty acid esters of ethoxylated sorbitans; polyethylene glycol-polypropylene glycol block copolymers, such as Pluronic®, and Pluronic R® surfactants sold by BASF-Wyandotte Corp. ("BASF"), Wyandotte, Mich.; Tetronic® and Tetronic R® surfactants sold by BASF, ethoxylated branched aliphatic diols such as Surfynol® surfactants sold by Air Product & Chemicals, Inc. Allentown, Pa; ethoxylated aliphatic alcohols and carboxylic acids; polyethylene glycol diesters of fatty acids; polyalkyleneoxide polysiloxanes; and mixtures thereof.

Suitable anionic surfactants are dialkyl sulfosuccinate, alkylarylsulfonate, fatty alcohol sulfate, paraffin sulfonate, alkyl sarcosinate, alkyl isethionate salts having suitable cations, e.g., sodium, potassium, alkanol ammonium, etc., and mixtures thereof. Suitable amphoteric surfactants are the betaines.

Also suitable are surfactants that have the hydrophilic groups situated between hydrophobic chains, such as Pluronic R® surfactant, Surfynol® surfactants, polyethylene glycol diesters of fatty acids, fatty acid esters of ethoxylated sorbitans, dialkyl sulfosuccinate, di($C_8$–$C_{12}$ alkyl)di(C1–C2 alkyl)ammonium halides, and mixtures thereof; or surfactants which have the hydrophobic chains situated between hydrophilic groups, such as Pluronic® surfactant; and mixtures thereof. Mixtures of the surfactants disclosed above may also be used.

Preferred surfactants for use in the present invention are surfactants which do not have a high level of interaction with the cyclodextrin, thus optimizing the odor absorbing capability of cyclodextrin. Extensive interaction is not desirable as it may diminish the ability of the cyclodextrin to complex with odor causing compounds and the ability of the surfactant to blend the oil and water phases.

Therefore, preferred surfactants optimize both the odor absorbing characteristic of cyclodextrin and the blending ability of the surfactant. Such surfactants, when added to an aqueous cyclodextrin solution, provide a surfactant/cyclodextrin solution which demonstrate odor absorption similar to the same cyclodextrin solution without the surfactant. Not desirable are surfactants which, when added to an aqueous cyclodextrin solution, provide a surfactant/cyclodextrin solution which demonstrate odor absorption similar to pure water.

Preferred surfactants can be identified using the procedure which follows. First, within an equilibrium chamber, a paper membrane is sealed to a test cell and wetted with a test sample mixture; or, for purposes of establishing a water control and a cyclodextrin control, the membrane is wetted with water or aqueous cyclodextrin. Test sample mixtures comprise mixtures of a solution of aqueous cyclodextrin and a surfactant or a combination of surfactants. Second, an odor causing challenge compound is injected into the equilibrium chamber and allowed to equilibrate through the paper membrane. The odor causing challenge compounds selected should be those which uncomplexed cyclodextrin is capable of absorbing such as isovaleric acid. Third, after a finite time air in the equilibrium chamber enveloping the test cell is pulled through a Drager tube, which results in a color change within the chamber. (Drager tubes are commercially available from Lab Safety, Danesville, Wis.). The distance of color movement up the Drager tube corresponds to the remaining (or uncomplexed) concentration of odorous material within the Drager tube. Replicates of this entire procedure are performed and averages are taken. Any similar procedure such as Gas Chromatograph Head Space Analysis may also be used.

The results from each test sample mixture are then compared to the results of the water control and the cyclodextrin control. As used herein, the phrase "odor capture" refers to the amount of cyclodextrin which complexes with the challenge compound. Thus, a high level of odor capture results in a low level of remaining challenge compound. The surfactant should provide a surfactant/cyclodextrin solution which demonstrates more odor capture than the water control. Preferred surfactants provide a surfactant/cyclodextrin solution which demonstrates no less than about 25%, more preferred no less than about 50%, and even more preferred no less than about 75%, of the level of odor capture as the cyclodextrin control. Most preferred surfactants provide about the same level of odor capture as the cyclodextrin control.

Additionally, it is preferable for formation of oil-in-water emulsions that the selected surfactant have a hydrophilic/lipophilic balance ("HLB") of about 8–18. The term HLB is known in the art, for example in U.S. Pat. No. 2,677,700 to Jackson et al., issued May 4, 1954, and incorporated herein by reference. Because of the uniqueness of many of the surfactants mentioned below, they will demonstrate lipophilic behavior different from hydrocarbon lipophiles. Consequently, the HLB values may not correlate exactly with the HLB values for ethylene oxide/hydrocarbon surfactants. Overall, the preferred surfactants for use herein include block copolymers of ethylene oxide and/or propylene oxide and polyalkyleneoxide polysiloxanes. Most preferred are mixtures of at least one of each of block copolymers of ethylene oxide and/or propylene oxide and polyalkyleneoxide polysiloxanes.

Block polyoxyethylene-polyoxypropylene polymeric compounds which are compatible with most cyclodextrins include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Block polymer surfactant compounds designated Pluronic® and Tetronic® are commercially available from the BASF-Wyandotte Corp.

Typical block copolymers of ethylene oxide and/or propylene surfactants include:

Pluronic® surfactants: $H(EO)_n(PO)_m(EO)_nH$;
Reverse Pluronic® surfactants: $H(PO)_n(EO)_m(PO)_nH$;

Tetronic® surfactants:

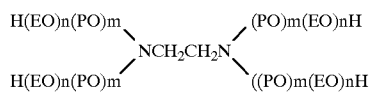

and/or

Reverse Tetronic® surfactants:

wherein EO is an ethylene oxide group, PO is a propylene oxide group, and n and m are numbers that indicate the average number of the groups in the surfactants. The average molecular weight of the polyoxypropylene polymers in the mixture is between about 900 to about 25,000 and the oxyethylene groups constitute between about 10 to about 90 weight percent of the oxyethylene/oxypropylene mixture. Non-limiting examples of surfactants useful herein having an HLB of about 8 to 18 include: Pluronic® surfactants L10, L43, L44, L63, L64, L65, P75, P84, P85, P103, P104, P105, P123, and mixtures thereof; Reverse Pluronic® surfactants 10R5, 17R4,17R8, 22R4,25R4, 25R5, 25R8, and mixtures thereof; Tetronic® surfactants: 304, 504, 704, 707, 904, 1104, 1304, 1504, and mixtures thereof; and Reverse Tetronic® surfactants 50R4, 50R8, 70R4, 90R8, 110R7150R8, and mixtures thereof; and mixtures thereof.

More detailed examples of the aforementioned surfactants and methods of making them are described in U.S. Pat. No. 2,674,619, Lundsted et al., issued Apr. 6, 1954; U.S. Pat. No. 3,036,118, Jackson et al., issued May 22, 1962; and U.S. Pat. No. 2,979,528, Lundsted et al., issued Apr. 11, 1961; all incorporated herein by reference in their entireties.

Polyalkyleneoxide polysiloxanes are defined by the general formula:

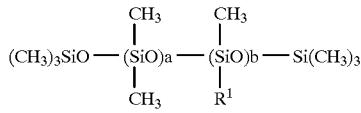

wherein a+b are from about 1 to about 50, preferably from about 3 to about 30, more preferably from about 10 to about 25, and $R^1$ is mainly one or more random or block poly(ethyleneoxide/propyleneoxide) copolymer groups having the general formula:

wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group. Examples of such compounds suitable herein include: Silwet® L-7600, L-7602, L-7604, L-7605, L-7657, and mixtures thereof; all commercially available from OSi Specialties, Endicott, N.Y.

The molecular weight of the oxyalkylene group ($R^1$) is less than or equal to 10000. Preferably, the molecular weight of the oxyalkylene group is less than or equal to about 8000, and most preferably ranges from about 300 to 5000. Thus, the values of c and d can be those numbers which provide molecular weights within these ranges. However, the number of oxyethylene units ($—C_2 H_4 O$) in the polyoxyalkylene groups ($R^1$) must be sufficient to render the polyalkyleneoxide polysiloxane water dispersible or water soluble. It is understood that when c is a positive number, the oxyethylene and oxypropylene units ($—C_3 H_6O$) can be distributed randomly throughout the polysiloxane chain or in respective blocks of oxyethylene and oxypropylene units or a combination of random and block distributions. The preparation of polyalkyleneoxide polysiloxanes is well known in the art. Such compounds can be prepared according to the procedure set forth in U.S. Pat. No. 3,299,112, incorporated herein by reference.

The total surfactant level used in the present compositions is from about 0.05% to about 15%, more preferably from about 0.1 % to about 12%, by weight of the composition. If a hydrophobic antimicrobial agent is included, more surfactant(s) should be included, typically from about 0.5% to about 10%, by weight of the composition.

Perfume Composition

The present invention contains a hydrophilic, volatile perfume composition comprising perfume ingredients. The hydrophilic perfume composition is volatile and fleeting such that the perfume is effusive and noticeable when the product is first used, but its odor impact is substantially diminished when the treated surface, e.g., skin, is dry. Preferred are perfume ingredients which are both hydrophilic and volatile.

The perfume composition is one which is safe for use on skin. The term "safe for use on skin", as used herein, means that the composition provides the desired benefit without undue adverse side effects.

A volatile and hydrophilic perfume ingredient is characterized by its boiling point ("B.P.") and its octanol/water partition coefficient ("P"). The boiling points of many perfume ingredients are given in, e.g., "Perfume and Flavor Chemicals (Aroma Chemicals)," Steffen Arctander, published by the author, 1969, incorporated herein by reference. The octanol/water partition coefficient of a perfume ingredient is the ratio between its equilibrium concentrations in octanol and in water. Since the partition coefficients of the preferred perfume ingredients have high values, they are more conveniently given in the form of their logarithm to the base 10, logP. LogP values which are calculated are referred to as "CLogP". ClogP values are readily calculated from a program called "CLOGP" which is available from Daylight Chemical Information Systems, Inc., Irvine Calif. Octanol/water partition coefficients are described in detail in U.S. Pat. No. 5,578,563, to Trinh, issued Nov. 26, 1996, incorporated herein by reference in its entirety. The preferred perfume ingredients have a B.P., determined at the normal, standard pressure of about 760 mm Hg, of about 260° C. or lower, preferably less than about 250° C., and a ClogP or an experimental logP, of less than about 3.5, and preferably of less than about 3.0.

Non-limiting examples of preferred hydrophilic, volatile perfume ingredients are allyl caproate, amyl acetate, amyl propionate, anisic aldehyde, anisole, benzaldehyde, benzyl acetate, benzyl acetone, benzyl alcohol, benzyl formate, benzyl isovalerate, benzyl propionate, beta gamma hexenol, camphor gum, laevo-carveol, d-carvone, laevo-carvone, cinnamyl formate, cis-jasmone, cis-3-hexenyl acetate, cuminic alcohol, cuminic aldehyde, Cyclal C, dimethyl benzyl carbinol, dimethyl benzyl carbinyl acetate, ethyl acetate, ethyl acetoacetate, ethyl amyl ketone, ethyl benzoate, ethyl butyrate, ethyl hexyl ketone, ethyl phenyl acetate, eucalyptol, fenchyl alcohol, flor acetate (tricyclo decenyl acetate), frutene (tricyclo decenyl propionate), geraniol, hexenol, hexenyl acetate, hexyl acetate, hexyl formate, hydratropic alcohol, hydroxycitronellal, isoamyl alcohol, isomenthone, isopulegyl acetate, isoquinoline, ligustral, linalool, linalool oxide, linalyl formate, menthone, methyl acetophenone, methyl amyl ketone, methyl anthranilate, methyl benzoate, methyl benzyl acetate, methyl eugenol, methyl heptenone, methyl heptine carbonate, methyl heptyl ketone, methyl hexyl ketone, methyl phenyl carbinyl acetate, methyl salicylate, nerol, nonalactone, octalactone, octyl alcohol (octanol-2), para-cresol, para-cresyl methyl ether, para-methyl acetophenone, phenoxy ethanol, phenyl acetaldehyde, phenyl ethyl acetate, phenyl ethyl alcohol, phenyl ethyl dimethyl carbinol, prenyl acetate, propyl butyrate, pulegone, rose oxide, safrole, terpineol, and viridine.

Examples of other hydrophilic, volatile perfume ingredients useful herein are allyl heptoate, anethol, carvacrol, cinnamic alcohol, citral, citronellol, citronellyl nitrile, cyclohexyl ethyl acetate, dihydro myrcenol, ethyl methyl phenyl glycidate,eugenol, fenchyl acetate, gamma-nonalactone, geranyl acetate, geranyl formate, geranyl nitrile, hexenyl isobutyrate, indole, alpha-ionone, isobornyl acetate, isobutyl benzoate, isononyl alcohol, isomenthol, isopulegol, linalyl acetate, methyl chavicol, methyl-N-methyl anthranilate, neral, neryl acetate, nonyl aldehyde, para-isopropyl phenylacetaldehyde, para-methoxy acetophenone, phenyl hexanol, terpinyl acetate, and veratrol.

The hydrophilic, volatile perfume composition is at a level of from about 0.004% to about 2%, preferably from about 0.006% to about 1%, and more preferably from about 0.007% to about 0.2%, by weight of the environmental odor control composition. The hydrophilic, volatile perfume composition comprises at least 4 different hydrophilic, volatile perfume ingredients, preferably at least 5 different hydrophilic, volatile perfume ingredients, more preferably at least 6 different hydrophilic, volatile perfume ingredients, and even more preferably at least 7 different hydrophilic, volatile perfume ingredients.

Furthermore, the hydrophilic, volatile perfume composition contains at least about 50 wt. % of hydrophilic, volatile perfume ingredients, preferably at least about 55 wt. % of hydrophilic, volatile perfume ingredients, more preferably at least about 60 wt. % of hydrophilic, volatile perfume ingredients, and even more preferably at least about 70 wt.% of hydrophilic, volatile perfume ingredients. Most common perfume ingredients which are derived from natural sources are composed of a multitude of components. When each such material is used in the formulation of hydrophilic, volatile perfume compositions of the present invention, it is counted as one ingredient, for the purpose of defining the invention. Synthetic reproductions of such natural perfume ingredients are also often comprised of a multitude of components and are counted as one ingredient for the purpose of defining the invention.

Some of the hydrophilic, volatile perfume ingredients can optionally be replaced by hydrophilic, residual perfume ingredients. The optional hydrophilic, residual perfume ingredients have a B.P., measured at the normal, standard pressure, higher than about 260° C., and an experimental logP or ClogP of less than about 3.5. Thus, when a perfume composition is composed of some preferred hydrophilic, volatile ingredients and some hydrophilic, residual ingredients, the perfume effect is longer lasting when the product is used. Non-limiting examples of optional hydrophilic, residual perfume ingredients, useful herein are amyl benzoate, benzophenone, dihydro isojasmonate, isoeugenol, methyl cinnamate, methyl dihydrojasmonate, beta-methyl naphthyl ketone, 2-methoxy naphthalene, delta-nonalactone, vanillin, yara-yara, and mixtures thereof.

When hydrophilic, residual perfume ingredients are used in combination with the hydrophilic, volatile perfume ingredients in the perfume compositions, the weight ratio of hydrophilic, volatile perfume ingredients to hydrophilic, residual perfume ingredients is typically greater than about 1, preferably greater than about 1.3, more preferably greater than about 1.5, and even more preferably greater than about 2. In this case, the perfume compositions contain at least about 50 wt. % of the combined hydrophilic, volatile perfume ingredients and hydrophilic, residual perfume ingredients, preferably at least about 55 wt. % of the combined perfume ingredients, more preferably at least about 60 wt. % of the combined perfume ingredients, and even more preferably at least about 70 wt. % of the combined perfume ingredients.

In the perfume art, some auxiliary materials having no odor, or a low odor, are used, e.g., as solvents, diluents, extenders or fixatives. Non-limiting examples of these materials are ethyl alcohol, carbitol, dipropylene glycol, diethyl phthalate, triethyl citrate, isopropyl myristate, and benzyl benzoate. These materials may be used for solubilizing or diluting some solid or viscous perfume ingredients to improve handling and/or formulating. These materials are useful in the hydrophilic, volatile perfume compositions, but are not counted in the calculation of the limits for the definition/formulation of the hydrophilic, volatile perfume compositions of the present invention.

Hydrophobic perfume ingredients, which should be minimized in odor controlling compositions of the present invention, are those having a ClogP. of more than about 3.5. Normally, some hydrophobic perfume ingredients can be used in small amounts, e.g., to improve product odor.

Aqueous Carrier

The cyclodextrins useful in the methods of the present invention should be solubilized in and dispersed in an aqueous carrier. The dilute aqueous solution provides the maximum separation of cyclodextrin molecules on the skin and maximizes the chance that an odor molecule will interact with a cyclodextrin molecule. An aqueous carrier is also beneficial in that it provides a clean, convenient means for applying the cyclodextrin to the desired skin sites. Additionally, an aqueous carrier may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied.

The aqueous carrier of the present invention will typically comprise from about 80% to about 98% of the present invention's composition. Preferably the compositions comprise the aqueous carrier at from about 85% to about 95%, by weight of the composition.

Antimicrobial Preservative

The compositions may optionally but preferably contain solubilized, mild, water-soluble, antimicrobial preservatives which are effective for inhibiting and/or regulating microbial growth in the composition. Contamination of the compositions by microorganisms and subsequent microbial growth can result in unsightly or malodorous compositions. Similarly, microorganisms are typically found in cyclodextrin supplies and their growth in aqueous solutions is possible. The inclusion of the antimicrobial preservatives aids in increasing storage stability of the present invention. When included for preservative action, the water-soluble antimicrobials are present in an effective amount. The phrase "effective amount" of water-soluble antimicrobial preservative as used herein means a level sufficient to prevent spoilage, or prevent growth of microorganisms inadvertently added to the composition, for a specific period of time. If antimicrobial action on the skin is desired, the water-soluble antimicrobials must be present at a level effective to perform the preservative action discussed above and to kill and/or prevent growth of microorganisms on the skin.

Antimicrobials useful herein include biocidal and biostatic compounds (substances that kill microorganisms and/or regulate the growth of microorganisms). Suitable water-soluble antimicrobial preservatives have a solubility of 0.3% or greater. In addition, suitable preservatives are those which can come into contact with skin without high irritation potential. Preservatives suitable for use in the present compositions are fully described in *The Theory and Practice of Industrial Pharmacy*, by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include the following: sodium hydroxymethylglycinate (i.e. Suttocide® A., from Sutton Labs Chatham, N.J.), cyclic organic nitrogen compounds including imidazolidinedione compounds (such as dimethyloldimethylhydantoin i.e., Glydant® Plus from Lonza, Fair Lawn, N.J., diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

Preferred levels of preservative are from about 0.0001% to about 0.6%, more preferably from about 0.0002% to about 0.55%, most preferably from about 0.0003% to about 0.5%, by weight of the composition.

Hydrophobic Antibacterial Agents

Optionally, the compositions of the present methods may include hydrophobic antibacterial compounds to help destroy and/or control the amount of bacteria present on the skin, which aids in body odor control. However, hydrophobic antibacterial agents can form inclusion complexes with the cyclodextrin molecules and compete with the malodorous molecules for the cyclodextrin cavities, thus rendering the cyclodextrins ineffective as odor controlling actives. To account for this, the level of cyclodextrin may be increased as desired. Hydrophobic antibacterials useful in the present invention include triclosan, triclocarbon, eucalyptol, menthol, methylsalicylate, thymol, and mixtures thereof. Preferred are triclosan and triclocarbon. When included in the present compositions, the hydrophobic antibacterials may be at a level of from about 0.1% to about 1.5% and preferably from about 0.1% to about 0.3%, by weight of the composition.

ph

Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid sodium hydroxide and hydrochloric acid are useful. Some of the effectiveness of these ingredients may be lost as they complex with the cyclodextrin, so care is taken in formulating to adjust for that. Other optional buffers appear in *The Theory and Practice of Industrial Pharmacy*, Lachman, Lieberman and Kanig, Third Edition, incorporated herein by reference.

Other Components

The compositions may also optionally comprise low molecular weight polyols. The phrase "low molecular weight polyols", as used herein, refers to linear organic compounds with more than one alcohol functional group per molecule wherein the molecular weight is less than 95. Low molecular weight polyols with relatively high boiling points, as compared to water, such as propylene glycol and glycerol are preferred ingredients for improving environmental malodor control performance of the present compositions. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

The present compositions can also optionally contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. Nos. 4,325,939, issued Apr. 20, 1982 and 4,469,674, issued Sep. 4, 1983, to N. B. Shah, et al., both of which are incorporated herein by reference in their entireties. Highly-ionized and water soluble zinc salts, such as zinc chloride, provide the best source of zinc ions. The zinc salt, zinc phenolsulfonate, is preferred for use in the skin composition of the present invention; although others may also fall within the scope of the present invention. However, care must be taken in selecting zinc salts, as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor.

When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon. While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. When these salts are added to the composition of the presalts not be present is preferred that incompatible metal salts not be present in the invention. Preferably, when these salts are used, the composition should be essentially free of zinc and other incompatible metal ions, e.g., Ca, Fe, etc. which form water-insoluble salts.

Aminocarboxylic acid chelating agents such as ethylenediaminetetraacetic acid (EDTA) can optionally be added to the composition of the present invention in order to enhance the activity of the water-soluble, antimicrobial preservative. When a chelating agent is added to the composition of the present invention, it is typically present at a level of from about 0.001% to about 0.3%, preferably from about 0.01% to about 0.2% by weight of the composition.

Zeolites can also be used in the present invention. A preferred class of zeolites are characterized as "intermediate" silicate/aluminate zeolites, particularly for use in absorbing amine-type odors. "High" zeolites are preferred for control of sulfur-containing odors, e.g., thiols, mercaptans. Zeolites are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dye levels that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green no. 5, 6 & 8, D&C yellow no. 7, 8, 10 & 11, D&C violet no. 2, FD&C blue No. 1 & 2, FD&C green no.3, FD&C yellow no. 5 & 6, and mixtures thereof.

Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine, aluminum-zirconium pentachlorohydrate, aluminum sesquichlorohydrate, or aluminum chlorhydrate and mixtures thereof.

Process of Making Compositions

The compositions may be prepared by oil-in-water emulsion techniques such as are commonly known in the art. Examples of such techniques are described in *Remington's Pharmaceutical Science*, Eighteenth Edition, pp. 304–306, 1990, incorporated herein by reference. The present compositions also may be prepared by a process comprising the steps of: Making a mixture by mixing a surfactant(s) and an oil phase until homogenous and adding an aqueous phase with mixing until the mixture is homogenous. Making a perfume mixture by mixing the first mixture with a perfume composition (alternatively the perfume composition could be added and mixed during the making of the first mixture). Making a solution by adding cyclodextrin with an aqueous phase with mixing until the cyclodextrin dissolves. Making a second mixture by mixing the solution with the perfume composition until the second mixture is homogenous. Where desired, the second mixture may be diluted by adding an aqueous phase with mixing until homogenous. Where hydrophobic antimicrobials also comprise the compositions, the process of making the mixture in the first step additionally comprises adding a premix with mixing to the surfactant(s) and the oil phase until homogenous, wherein the premix is prepared by mixing a hydrophobic antimicrobial with a surfactant(s) until the premix is homogenous. The term "homogenous", as used herein, means a uniformly dispersed solution. Homogeneity is indicated by a substantially smooth, lump-free and uniform appearing composition. A stable emulsion remains homogeneous over a given period which is determined by the required shelf life of the composition.

As an alternative to making the mixture by mixing a surfactant(s), an oil phase, and an aqueous phase; an emulsion concentrate comprising a surfactant(s), an oil phase, and a minimal amount of aqueous carrier may be used. Emulsion concentrates useful in the present invention will be from about a 3-fold to about a 20-fold concentrate. The concentrated emulsion may then be diluted by adding aqueous carrier followed by addition of the remaining ingredients as discussed above. A suitable method of forming an emulsion concentrate is described in U.S. Pat. No. 5,043,155, to Puchalski et. al, issued Aug. 27, 1991. An example of an emulsion concentrate useful in the present invention is Dow Corning® 365, 35% Dimethicone Emulsion.

Variations to the above process of making should be readily apparent to those having ordinary skill in the art. For instance, the mixture could be made in one step by addition and mixing of each of the ingredients. Alternatively, less than all of the ingredients may be pre-combined for subsequent combination with other ingredients or with other pre-combined ingredients to form the composition. The perfume composition could be added along with the cyclodextrin or other ingredients, or in a separate, final mixing step.

Equipment suitable for forming the mixtures and emulsion may be selected from those which are known or become known in the art. For example, suitable apparatii include dual propeller blade mixers and sonifers. A turbine mixer and an in-line homogenizer using tandem rotor-stators, as described in the above-referenced U.S. Pat. No. 5,043,155, may also be used.

The resultant emulsion containing the ingredients in their total amounts has a preferred viscosity at room temperature (i.e., 20°–25° C.) in the range of from about 10 to about 200 centipoise more preferably from about 15 to about 150 centipoise; most preferably from about 20 to about 100 centipoise.

Since the compositions of the present invention are applied directly to skin and/or hair, various applicators are useful for delivering the compositions to the entire body for maximum environmental odor control. For example, the compositions are preferably deposited on a paper product such as a wipe which later is contacted with the skin to transfer the composition to the skin.

Any wipe structures and/or methods of making the wipe structures commonly known in the art may be used in the present invention. The wipe comprises a flexible dispensing means. The term "flexible dispensing means", as used herein, includes papers, cloths, non-wovens, films, foams, foam sheets, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic in the present invention are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references are incorporated herein by reference in their entireties.

Techniques for combining the wipe substrates with the present compositions are well known in the art. Examples of common methods of combining the compositions to the wipe substrate may involve coating, immersing, dipping, or spraying the wipe substrate with the composition of the present invention. The compositions are added to the wipe substrate at level sufficient to provide the desired odor control and/or other desired skin benefits of the present invention. A convenient method of combining the compositions with the chosen substrate is to place the substrate inside an open package which will ultimately house the finished product until use. The composition is poured onto the substrate and allowed to distribute throughout. It is preferred that the homogenous composition is poured onto each wipe individually rather than onto a stack of wipes. The package is then closed and the wipes ready for use. Packages suitable for use herein are any packages commonly known in the art and include resealable packages, and those suitable for one time use.

The composition of the present invention can also be delivered as a liquid via a spray dispenser or a bottle. Preferred is a manually activated spray dispenser to avoid the use of aerosols which may be irritating to sensitive areas of the body. Spray dispensers useful in the present invention are described more fully in U.S. Pat. No. 5,534,165 which is incorporated herein by reference in its entirety.

The following non-limiting examples illustrate the formulations and methods of use of the present invention.

| Ingredients | Wt. % |
|---|---|
| PERFUME COMPOSITION A | |
| Anisic aldehyde | 2.53 |
| Benzyl acetate | 5.05 |
| Benzyl propionate | 1.26 |
| Beta gamma hexanol | 0.50 |
| Cinnamic alcohol | 1.27 |
| cis Jasmone | 0.50 |
| Dihydro myrcenol | 6.32 |
| Dimethyl benzyl carbinyl acetate | 3.78 |
| Eucalyptol | 1.77 |
| Geraniol | 12.63 |
| Geranyl nitrile | 3.03 |
| Hydroxycitronellal | 7.57 |
| alpha Ionone | 3.04 |
| Iso bornyl acetate | 3.78 |
| Ligustral | 0.51 |
| Linalool | 6.31 |
| Linalyl acetate | 2.53 |
| Methyl benzoate | 0.50 |
| Methyl dihydro jasmonate | 7.58 |
| Phenyl ethyl acetate | 1.26 |
| Phenyl ethyl alcohol | 14.90 |
| Phenyl hexanol | 3.78 |
| Rose oxide | 0.76 |
| Terpineol | 7.58 |
| Vanillin | 1.26 |
| PERFUME COMPOSITION B | |
| Allyl caproate | 0.8 |
| Amyl acetate | 0.4 |
| Anisic aldehyde | 0.8 |
| Benzyl acetate | 5.0 |
| Benzyl propionate | 2.1 |
| beta gamma Hexanol | 0.4 |
| Cinnamic alcohol | 1.4 |
| Citral | 5.1 |
| Citronelly nitrile | 2.1 |
| Dihydro myrcenol | 5.0 |
| Dimethyl benzyl carbinyl acetate | 2.1 |
| Eucalyptol | 1.3 |
| Fenchyl alcohol | 1.7 |
| Flor acetate | 6.1 |
| Frutene | 3.1 |
| Geraniol | 4.2 |
| Geranyl nitrile | 3.0 |
| Hexanol | 0.4 |
| Iso bornyl acetate | 1.3 |
| laevo Carvone | 0.4 |
| Linalool | 12.5 |
| Methyl anthranilate | 2.9 |
| Methyl beta-naphthyl ketone | 4.2 |

-continued

| Ingredients | Wt. % |
| --- | --- |
| Methyl dihydro jasmonate | 20.7 |
| Methyl heptine carbonate | 0.1 |
| Nonyl aldehyde | 0.8 |
| Octyl alcohol | 2.1 |
| para Methoxy acetophenone | 1.3 |
| Phenyl ethyl alcohol | 8.3 |
| Camphor gum | 0.4 |

EXAMPLES I, II, and III

|  | Example I | Example II | Example III |
| --- | --- | --- | --- |
| Pluronic ® L-44 |  | 0.15 | 0.30 |
| Pluronic ® L-43 | 0.20 |  |  |
| Silwet ® L-7657 |  |  | 0.30 |
| Silwet ® L-7605 |  | 0.15 |  |
| Silwet ® L-7600 | 0.20 |  |  |
| Dimethicone | 2.00 | 1.00 | 2.00 |
| Triclosan |  |  | 0.15 |
| Perfume composition* | 0.008 | 0.06 | 0.04 |
| Hydroxy Propyl Beta Cyclodextrin | 1.00 | 5.00 | 2.00 |
| Zinc Phenolsulfonate | 1.01 | 1.01 |  |
| Ascorbic Acid | 0.40 | 1.75 | 2.00 |
| Glydant ® Plus | 0.30 | 0.20 | 0.30 |
| Suttocide ® A |  | 0.25 | 0.50 |
| Propylene Glycol | 0.06 | 0.3 | 0.1 |
| Water | Balance | Balance | Balance |

*The perfume composition listed in Examples I–III can be any one of the preceding perfume composition examples A or B.

Alternatively, the hydroxy propyl beta cyclodextrin in the above examples could be substituted with other beta cyclodextrins, alpha-cyclodextrins, gamma-cyclodextrins, or mixtures of these cyclodextrins and/or their derivatives. Similarly, the examples could comprise other hydrophobic antimicrobials.

Prepare Examples I-III as follows: Prepare a premix by mixing triclosan with about ⅙, by weight, of total Pluronic® L and/or Silwet® L (Example III only). Prepare a first mixture by mixing about 1% of water, by total formula weight, with a perfume and surfactant(s). For Example III, preparing the first mixture also includes a final step of adding the premix with mixing. Using a sonifier, prepare a second mixture by adding dimethicone to the first mixture, then slowly adding about 1%–2% of water, by total formula weight. Prepare premix (a) by mixing hydroxypropyl beta cyclodextrin and about 1.5%–3% of water, by total formula weight; premix (b) by mixing zinc phenolsulfonate and about 2% of water, by total formula weight; premix (c) by mixing the ascorbic acid and about 2% of water by total formula weight; and premix (d) by mixing Glydant® Plus (and Suttocide® A) and propylene glycol. Using a homogenizer, add remaining water to the second mixture to create a third mixture. Add premixes (a), (b), (c), and (d) to the third mixture using the homogenizer.

Preparation for Application to Skin

The solutions of the present invention, such as those formed from the examples may be loaded onto a wipe or poured into a spray device or poured directly onto the skin or cloth of the user's choosing for convenient application to the skin and/or hair.

To prepare wipes: Place dry fabric or wipe substance inside an open package which will ultimately contain the finished product. Where the composition comprises dimethicone, the mixture should once again be mixed vigorously to obtain a homogenous solution. Pour the composition onto the fabric to distribute throughout. Close the package for storage until consumer use.

To prepare spray: Pour the composition into the selected spray package. Close the package for storage until consumer use.

Example IV

A man is cooking fish and a spicy sauce requiring the dicing of garlic, onions, and various peppers. He is told that his hands and hair smell of these food odors and he wants to remove these odors from his body. The man rubs his hands and hair with wipes containing the composition in Example I. Each wipe deposits about 0.05 grams of environmental odor-absorbing composition on the skin and hair. The man notices less odor after using the wipes.

Example V

A woman finds that after she smokes a cigarette during a break at work, her hands and face smell of smoke and tobacco. She applies the composition from Example II via a hand-held trigger-spray bottle. (She deposits about 2.0 grams of environmental odor-absorbing composition on the skin). She sprays the composition on her face and hands and the composition removes the residual smoke and tobacco odors which she found so disagreeable. This woman notices less odor and feels more comfortable returning to her desk after using the spray.

Example VI

A man, on his way to an important meeting, stops to buy gasoline for his car. As he is filing the gas tank, gasoline splashes on his hands. The man wipes his hands on a paper towel but the gasoline odor remains on his hands. The man removes a small bottle from his gym bag which contains the composition of Example III. He opens the bottle and pours some of the composition on his hands, delivering roughly about 0.5 grams of the environmental odor-absorbing composition. He then smells his hands and notices that the gasoline odor is no longer present.

What is claimed:

1. A method of controlling environmental malodors on skin comprising the application to skin of a composition comprising:
    a. from about 0.1% to about 5%, by weight of the composition, of solubilized, water-soluble, uncomplexed cyclodextrin;
    b. an aqueous carrier;
    c. from about 0.1% to about 36%, by weight of the composition, of an oil phase selected from the group consisting of emollients, moisturizers, and skin protectants;
    d. one or more surfactants; and
    e. from about 0.004% to about 2%, by weight of the composition, of a hydrophilic, volatile perfume composition.

2. The method of claim 1 wherein the composition is deposited on a wipe which comprises a flexible dispensing means.

3. The method of claim 2 wherein the perfume composition comprises at least 5 different hydrophilic, volatile perfume ingredients wherein each ingredient has a boiling point of about 260° or lower, and a ClogP of less than about 3.5.

4. The method of claim 3 wherein the composition further comprises one or more water-soluble antimicrobial preservatives.

5. The method of claim 4 wherein the one or more surfactants each has a hydrophilic/lipophilic balance of about 8 to 18 and wherein each surfactant, when combined with an aqueous cylcodextrin solution, provides no less than about 25% a level of odor capture as an aqueous cyclodextrin solution.

6. The method of claim 5 wherein the composition further comprises one or more optional components selected from the group consisting of low molecular weight polyols; hydrophobic antimicrobials; zinc salts; water-soluble polymers; soluble carbonate and/or bicarbonate salts; chelating agents; zeolites; activated carbon; and mixtures thereof.

7. A method of controlling environmental malodors on skin comprising the application to skin of a composition comprising:
   a. from about 0.1% to about 5%, by weight of the composition, of solubilized, water-soluble, uncomplexed cyclodextrin;
   b. an aqueous carrier;
   c. from about 0.1% to about 36%, by weight of the composition, of an oil phase selected from the group consisting of emollients, moisturizers, and skin protectants;
   d. one or more surfactants each having a hydrophilic/ lipophilic balance of about 8 to 18 and wherein each surfactant, when combined with an aqueous cylcodextrin solution, provides no less than about 50% a level of odor capture as an aqueous cyclodextrin solution;
   e. a hydrophobic antimicrobial; and
   f. from about 0.004% to about 2%, by weight of the composition, of a hydrophilic, volatile perfume composition comprising one or more hydrophilic, volatile perfume ingredients wherein each ingredient has a boiling point of about 260° or lower, and a ClogP of less than about 3.5.

8. The method according to claim 7 wherein the one or more surfactants are selected from the group consisting of block copolymers of polyoxyethylene-polyoxypropylene, polyalkyleneoxide polysiloxanes, and mixtures thereof.

9. The method according to claim 8 wherein the one or more surfactants each has a hydrophilic/lipophilic balance of about 8 to 18 and wherein each surfactant, when combined with an aqueous cylcodextrin solution, provides no less than about 75% a level of odor capture as an aqueous cyclodextrin solution.

10. The method according to claim 9 wherein the perfume composition comprises at least 7 different hydrophilic, volatile perfume ingredients.

11. The method according to claim 10 wherein the hydrophobic antimicrobial is selected from the group consisting of triclosan, triclocarbon, eucalyptol, menthol, methylsalicylate, and thymol; and is present at a level of from about 0.1% to about 1.5% by weight of the composition.

12. The method of claim 11 wherein the composition further comprises one or more optional components selected from the group consisting of low molecular weight polyols; water-soluble antimicrobial preservatives; zinc salts; water-soluble polymers; soluble carbonate and/or bicarbonate salts; chelating agents; zeolites; activated carbon; and mixtures thereof.

13. The method of claim 12 wherein the composition is deposited on a wipe which comprises a flexible dispensing means.

14. The method of claim 12 wherein the composition is delivered as a liquid by a spray bottle.

15. A method of controlling environmental malodors on skin comprising the application to skin of a composition comprising:
   a. from about 0.1% to about 5%, by weight of the composition, of solubilized, water-soluble, uncomplexed cyclodextrin selected from the group consisting of hydroyxpropyl beta-cyclodextrin, methylated beta-cyclodextrins, and mixtures thereof;
   b. an aqueous carrier;
   c. from about 0.1% to about 36%, by weight of the composition, of an oil phase selected from the group consisting of emollients, moisturizers, and skin protectants;
   d. one or more surfactants each having a hydrophilic/ lipophilic balance of about 8 to 18 and wherein each surfactant, when combined with an aqueous cylcodextrin solution, provides no less than about 50% a level of odor capture as an aqueous cyclodextrin solution;
   e. antimicrobials selected from the group consisting of a hydrophobic antimicrobial, a water-soluble hydrophilic antimicrobial preservative, and mixtures thereof;
   f. from about 0.004% to about 2%, by weight of the composition, of a hydrophilic, volatile perfume composition comprising one or more hydrophilic, volatile perfume ingredients wherein each ingredient has a boiling point of about 260° or lower, and a ClogP of less than about 3.5; and wherein the composition is deposited on a wipe which comprises a flexible dispensing means.

16. The method according to claim 15 wherein the one or more surfactants are selected from the group consisting of block copolymers of polyoxyethylene-polyoxypropylene, polyalkyleneoxide polysiloxanes, and mixtures thereof.

17. The method according to claim 16 wherein the hydrophobic antimicrobial is selected from the group consisting of triclosan, triclocarbon, eucalyptol, menthol, methylsalicylate, and thymol; and is present at a level of from about 0.1% to about 1.5% by weight of the composition.

18. The method of claim 17 wherein the composition further comprises one or more optional components selected from the group consisting of low molecular weight polyols; zinc salts; water-soluble polymers; soluble carbonate and/or bicarbonate salts; chelating agents; zeolites; activated carbon; and mixtures thereof.

* * * * *